US006447786B1

(12) United States Patent
Novick et al.

(10) Patent No.: US 6,447,786 B1
(45) Date of Patent: *Sep. 10, 2002

(54) **BLOCKING EXPRESSION OF VIRULENCE FACTORS IN *S. AUREUS***

(75) Inventors: Richard P. Novick, New York; Guangyong Ji, Elmhurst, both of NY (US); Ronald Beavis, Indianapolis, IN (US)

(73) Assignee: New York University, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/861,476

(22) Filed: May 22, 1997

Related U.S. Application Data

(63) Continuation-in-part of application No. 08/651,226, filed on May 22, 1996, now abandoned, which is a continuation-in-part of application No. 08/318,499, filed on Oct. 4, 1994, now abandoned.

(51) Int. Cl.⁷ ............................................. A61K 39/085
(52) U.S. Cl. .................... 424/243.1; 530/350; 530/300; 530/317; 530/327; 530/328; 530/329; 424/184.1; 424/185.1; 424/190.1; 435/69.1; 435/69.3
(58) Field of Search .................. 530/350, 300, 530/317, 327, 328, 329; 424/243.1, 184.1, 185.1, 190.1; 435/69.1, 69.3

(56) References Cited

FOREIGN PATENT DOCUMENTS

WO          WO9610579         4/1996

OTHER PUBLICATIONS

Soe et al. J. Virol. 1987, 61(12): 3968–3976.*
Fukuhara et al. 1993, Plant Molec. Biol. 21: 1121–1130.*
Moriyama et al. 1995, Mol Gen. Geret. 248:364–369.*
Vandenesch et al. 1993, FEMS Microbiol. Lett. 111:115–122.*
Janzon et al, 1989, Mol.Gen. Genet. 219:480–485.*
Novick et al. 1995, Mol. Gen. Genet. 248: 446–458.*
Naomi Balaban, et al., entitled "Autocrine Regulation Of Toxin Synthesis By Staphylococcus Aureus," *Proc. Natl. Acad. Sci.*, vol. 92, pp. 1619–1623, Feb. 1995.
R.P. Novick, et al., entitled "The agr P2 Operon: An Autocatalytic Sensory Transduction System In Staphylococcus Aureus," *Molecular & General Genetics (1995)* 248: 446–458.
Richard P. Novick, et al., entitled "Synthesis Of Staphylococcal Virulence Factors Is Controlled By A Regulatory RNA Molecule," *The EMBO Journal*, vol. 12, No. 10, pp. 3967–3975, 1993.
Eva Morfeldt, et al., entitled "Activation Of Alpha–Toxin Translation In Staphylococcus Aureus By the Trans–Encoded Antisense RNA, RNAIII," *The EMBO Journal*, vol. 14, No. 18, pp. 4569–4577, 1995.
Naomi Balaban, et al., entitled Translation of RNAIII, The Staphylococcus Aureus AGR Regulatory RNA Molecule, Can Be Activated By A 3'–End Deletion, *FEMS Microbiology Letters*, 133 (1995) 155–161.
Ambrose L. Cheung, et al., entitled "Cloning And Sequencing Of sarA Of Staphylococcus Aureus, A Gene Required For The Expression of agr", *Journal of Bacteriology*, Jul. 1994, p. 4168–4172, vol. 176, No. 13.
Francois Vandenesch, et al., entitled "A Temporal Signal, Independent Of agr, Is Required For hla But Not spa Transcription In Staphylococcus Aureus", *Journal of Bacteriology*, Oct. 1991, p. 6313–6320, vol. 173, No. 20.
Ji, et al., entitled "Cell Density Control Of Staphylococcal Virulence Mediated By An Octapeptide Pheromone", *Proceedings of The National Academy of Sciences, USA*, Dec. 1995, vol. 92, No. 6, pp. 12055–12059.

* cited by examiner

*Primary Examiner*—Jennifer E. Graser
(74) *Attorney, Agent, or Firm*—Amster, Rothstein & Ebenstein

(57) ABSTRACT

This invention provides peptides which inhibit agr transcription in *S. aureus* and thereby block the expression of virulence factors in *S. aureus*, pharmaceutical compositions comprising these peptides, as well as methods for treating or preventing an infection or disease caused by *S. aureus* using the peptides of the present invention.

17 Claims, 4 Drawing Sheets

COMPARISON OF PREDICTED AgrD SEQUENCES
IN S. AUREUS AND S. LUGDUNENSIS STRAINS

| | | | | |
|---|---|---|---|---|
| RN6390B | MNTLFNLFFD | FITGILKNIG | NIAAYSTCDF | IMDEVEVPKE | LTQLHE* | 46 aa |
| RN7690 | MNTLFNLFFD | FITGILKNIG | NIAAYSTCDF | IMDEVEVPKE | LTQLHE* | 46 aa |
| RN6607 | MNTLVNMFFD | FIIKLAKAIG | IVGGVNACSS | LFDEPKVPAE | LTNLYDK* | 47 aa |
| RN8463 | MKKLLNKVIE | LLVDFFNSIG | YRAAYINCDF | LLDEAEVPKE | LTQLHE* | 46 aa |
| S. lugd. | MNLLSGLFTK | GISAIFEFIG | NFSAQDICNA | YFDEPEVPQE | LIDLQRKQLI ESV* | 53 aa |

FIG. 2

BLOCKING EXPRESSION OF VIRULENCE FACTORS IN S. AUREUS

This application is a continuation-in-part of copending application Ser. No. 08/651,226, filed May 22, 1996, which is a continuation-in-part of application Ser. No. 08/318,499, filed Oct. 4, 1994, now abandoned the contents of which are incorporated by reference herein.

STATEMENT OF GOVERNMENT INTEREST

This invention was made under NIH Grant No. A1-R01-30138. As such, the Government has certain rights in the invention.

BACKGROUND OF THE INVENTION

*Staphylococcus aureus* (*S. aureus*) is Gram-positive, aerobic bacterial pathogen, distinguished from other staphylococcal species by the production of the enzyme coagulase. *Sa* is a normal inhabitant of the skin and mucous membranes of man and other animals and under certain circumstances invades the body, causing a wide variety of disease conditions ranging from superficial abscesses (boils and furuncles) to disfiguring and life-threatening deep infections such as endocarditis, pneumonia, osteomyelitis, septic arthritis, meningitis, post-operative wound infections, and septicemia. *Sa* also causes diseases such as toxic shock syndrome.

Like other Gram-positive pathogens, *Sa* causes disease chiefly through the production and secretion of injurious proteins. These injurious extracellular proteins, or virulence factors (VF), include toxins that damage or dissolve host cells, toxins that interfere with the immune system, and enzymes that degrade tissue components such as proteins, nucleic acids, lipids and polysaccharides.

In laboratory cultures, VF are produced and secreted at the end of the standard exponential growth phase, during a segment of the growth cycle known as the post-exponential phase. The production of VF is coordinately regulated and is thought to represent an attempt by the bacteria to generate new sources of nutrition at a time of rapidly diminishing resources. In the infected individual, this may include an attack on the host defenses that have been mobilized to ward off and contain the infection.

*Sa* infections are presently treated with antibiotics, which are natural or semisynthetic chemicals that kill or inhibit the growth of bacterial cells. Unfortunately, antibiotics have become less and less effective in treating *Sa* infections due to the acquired resistance of Sa to these antibiotics. Major nosocomial epidemics are now caused worldwide by strains of *Sa* that are resistant to most antibiotics. The antibiotic vancomycin is still effective in treating various strains of *Sa*, although there is a grave danger that those strains will soon acquire resistance to vancomycin from a closely related Gram-positive pathogen, *Enterococcus faecalis*.

Since there is little reason to expect the introduction of major new classes of antibiotics, there is an urgent need to develop new methods to control *Sa* infections, such as interference with the expression of VF. If the bacteria could be disarmed, it is believed that host defenses would do the rest.

In *S. aureus*, expression of virulence factors is controlled by a global regulator known as agr (Peng, H., et al. *J. Bacteriol.* 179: 4365–4372 (1988); Regassa, L. B., et al. *Infect. Immun.* 60: 3381–3383 (1992)). Agr is a genetic locus that contains several genes. Two of these, agrA and agrC, are thought to constitute a signal transduction (STR) pathway that responds to one or more external signalling molecules by activating the transcription of a third gene, agr-rnaIII (Kornblum, J., et al., in Molecular Biology of the Staphylococci, R. P. Novick, ed. (VCH Publishers, New York, 1990); Bourret, R. B., et al. *Annu. Rev. Biochem.* 60: 401–441 (1991)). The primary transcript of aqr-rnaIII, known as RNAIII, induces transcription of the 20 or more independent genes encoding virulence factors, thereby resulting in the synthesis of VF (Novick, R. P., et al. *EMBO Journal* 12(10): 3967–3975 (1993)).

It has been shown that laboratory-generated mutant strains of *Sa*, unable to express VF, exhibit greatly reduced virulence (Foster, et al. *Molecular Biology of the Staphylococci*, Editor: R. P. Novick, VCH Publishers, New York, pp. 403–420 (1990)). Interference with activation of the agr system would therefore afford a simple means of blocking the expression of VF, and thus interfere with the infective process. Raychoudhury, S. et al. *PNAS* 90:965–969 (1993) recently described the identification of synthetic chemical compounds that block the expression of alginate, a VF for the cystic fibrosis pathogen, *Pseudomonas aeruginosa*. It has not been shown, however, whether these chemicals would have any effect on *Sa*, or offer any potential clinical utility.

SUMMARY OF THE INVENTION

The present invention is based upon the discovery of peptides which interfere with the activation of rnaIII transcription and thus prevent expression of VF. Prevention of the expression of VF by *S. aureus* using peptides which inhibit activation of rnaIII transcription are expected to prevent or treat diseases caused by Staphylococcal infections. Finally, the peptides of the present invention, in addition to treating or preventing diseases or infection caused by *S. aureus*, also can be used in vitro for preventing colonization of *S. aureus*.

BRIEF DESCRIPTION OF THE FIGURES

FIG. 2 represents a comparison of the predicted AgrD sequences of *S. aureus* strains RN6390B (laboratory strain) (SEQ ID NO:5), RN7690 (clinical isolate) (SEQ ID NO:5), RN6607 (clinical isolate) (SEQ ID NO:6), RN8463 (clinical isolate) (SEQ ID NO:7), and *S. lugunensis* (SEQ ID NO:8). The underlined region of each sequence (SEQ ID NO:2, SEQ ID NO:2; SEQ ID NO:3; SEQ ID NO:4; and SEQ ID NO:1, respectively) corresponds to the identification of the activator peptide from RN6390B (SEQ ID NO:2) and the inhibitor peptide from *S. lugunensis* (SEQ ID NO:1).

and mid-exponential phase (MEP) cultured *S. aureus* strains RN6390B, RN6607 and RN8463. The RNAIII transcription was measured as described in Ji, G., et al. *PNAS USA* 92:12055–12059 (1995) with 10 mM Tris-HCl, pH 7.5 as the control.

Figure 1:
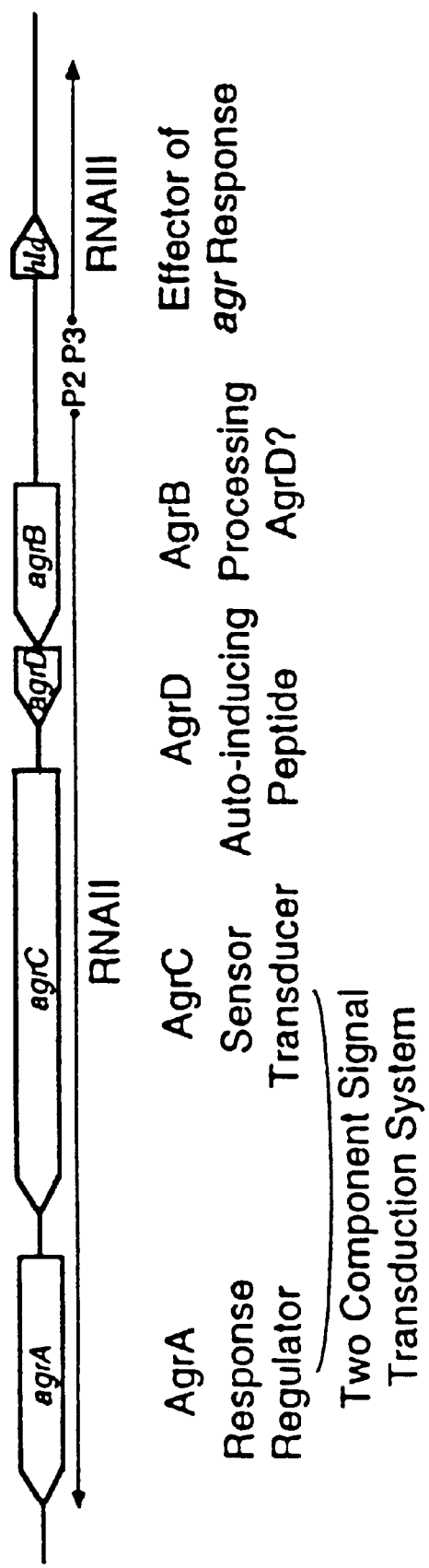
FIG. 1 represents the aqr locus of *S. aureus*. Schematic map of the agr locus showing the major transcripts RNAII and RNAIII (arrows) and the genes indicated by boxes.
Figure 3A:
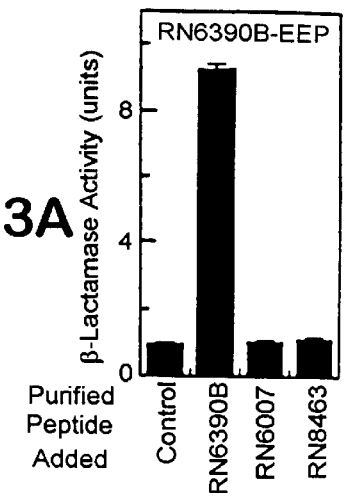
FIGS. 3A–3F represents the effects of purified peptide from *S. aureus* strains RN6390B, RN6607 and RN8463 on the RNAIII transcription of early exponential phase (EEP)
Figure 3B:
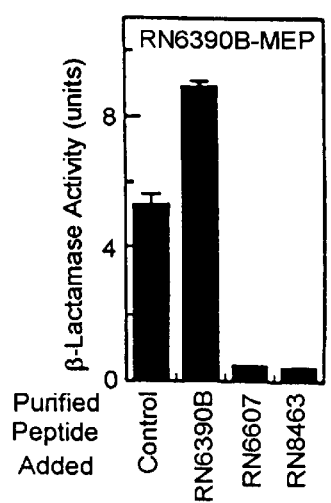
Figure 3C:
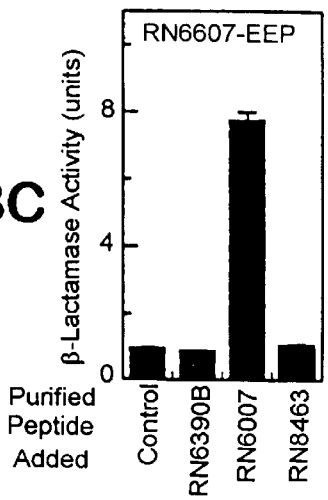
Figure 3D:
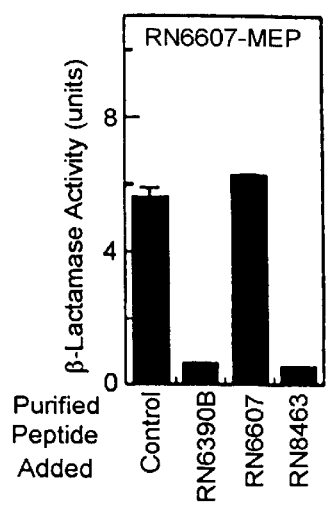
Figure 3E:
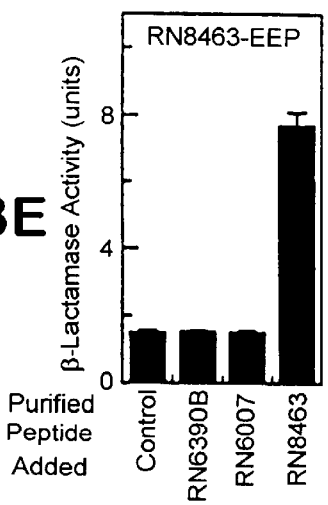
Figure 3F:
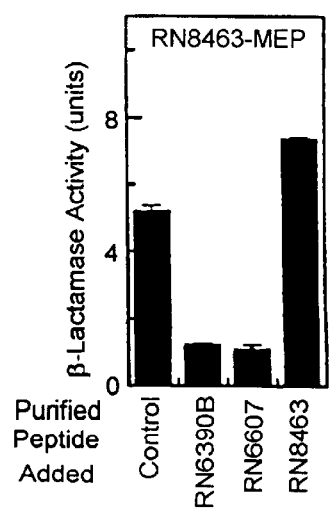
Figure 4B:
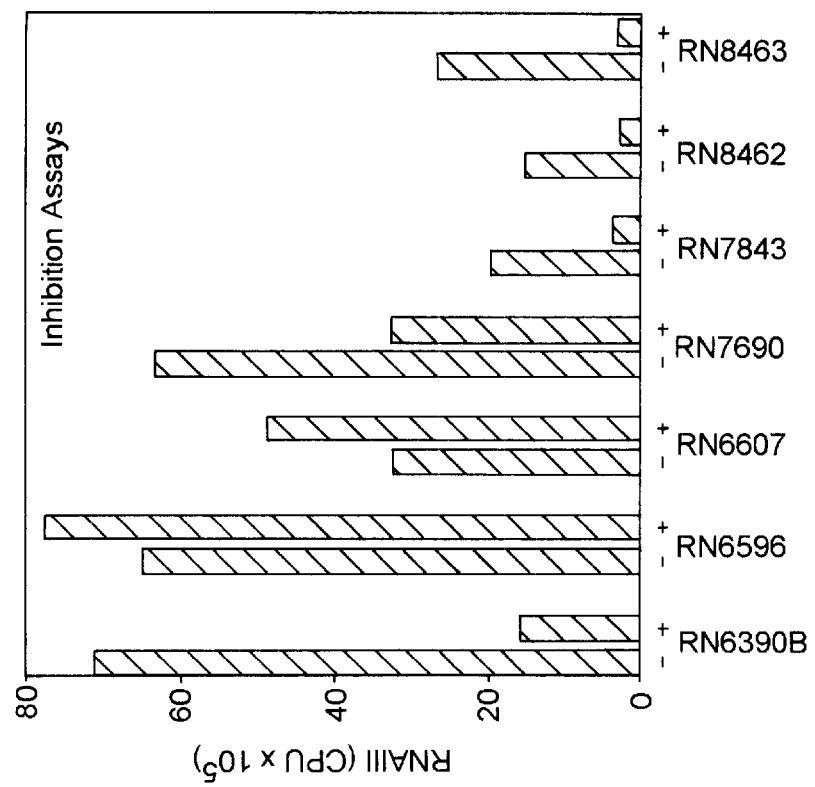
Figure 4A:
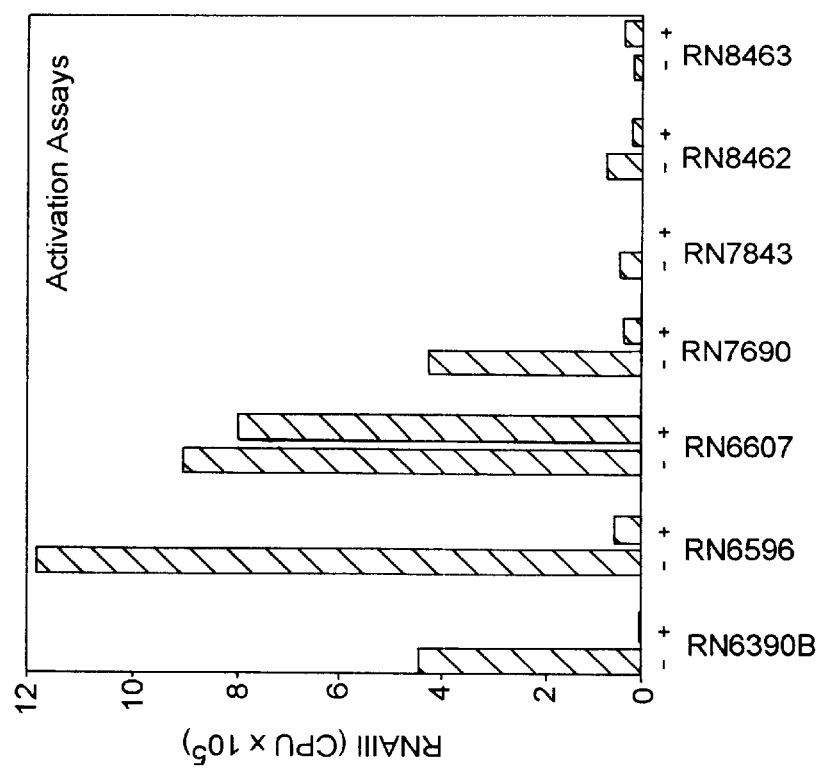

FIGS. 4A and 4B represent the effect of *S. luqdunensis* pheromone on the RNAIII transcription of various *S. aureus* strains: RN6390B (laboratory strain), RN6596 (laboratory strain), RN6607 (clinical isolate), RN7690 (clinical isolate), RN7843 (clinical isolate), RN8462 (TSST) and RN8463 (TSST). FIG. 4A, activation assays; FIG. 4B, inhibition assays.

DETAILED DESCRIPTION OF THE INVENTION

The present invention provides purified and isolated peptides which inhibit agr-rnaIII transcription in *S. aureus*. The peptides of the present invention are cyclic, comprise about six to about twelve amino acids in length, and include amino acid number 28 from the AgrD region of a staphylococci bacterium. As used herein, amino acid number 28 of the agrD region of a staphylococci bacterium corresponds to the "cysteine" shown in FIG. 2, which is believed to be conserved in the corresponding AgrD regions of various staphylococci bacterium. The staphylococci bacterium includes but is not limited to *S. aureus, S. capitis, S. caprae, S. carnosus, S. caseolyticus, S. epidermidis, S. haemolyticus, S. hominis, S. hvicus* subsp. *hyicus, S. hvicus* subsp. chromo, *S. kloosii, S. lentus, S. lugdunensis, S. sciuri, S. simulans* and *S. xylosus*.

The inhibitor peptides of the present invention include sequences corresponding to the native peptide from staphylococci bacterium, as well as analogues thereof which contain amino acid substitutions which also result in the peptides being able to inhibit agr-rnaIII transcription in *S. aureus*. The purified inhibitor peptides of the present invention may be isolated directly from staphylococci bacterium, recombinantly produced, or synthesized chemically using procedures known in the art. Preferably, the peptides are synthesized chemically. Specific examples of the inhibitor peptides include but are not limited to the following amino acid sequences: NH$_2$-Asp-Ile-Cys-Asn-Ala-Tyr-Phe-COOH (SEQ ID No:1), NH$_2$-Tyr-Ser-Thr-Cys-Asp-Phe-Ile-Met-COOH, (SEQ ID NO:2) NH$_2$-Gly-Val-Asn-Ala-Cys-Ser-Ser-Leu-Phe-COOH (SEQ ID NO:3and NH$_2$-Tyr-Ile-Asn-Cys-Asp-Phe-Leu-Leu-COOH (SEQ ID NO:4), wherein each peptide contains a cyclic thioester bond between the cysteine and the COOH end. The synthesis of peptides containing cyclic thioester bonds between the cysteine and the COOH end is within the purview of one skilled in the art. It is also within the confines of the present invention that the cyclic bond can be a bond other than a thioester bond, such as a disulfide bond, for example, which can be obtained by adding a cysteine residue at the carboxyl end, so long that such a modification results in a peptide having inhibitor activity.

The present invention also provides a peptide composition comprising one or more of the inhibitor peptides and a pharmaceutically or physiologically acceptable carrier. The carrier must be "acceptable" in the sense of being compatible with the other ingredients of the formulation and not deleterious to the recipient thereof. Examples of suitable pharmaceutical carriers include lactose, sucrose, starch, talc, magnesium stearate, crystalline cellulose, methyl cellulose, carboxymethyl cellulose, glycerin, sodium alginate, gum arabic, powders, saline, water, among others. The choice of carrier will depend upon the route of administration. The formulations may conveniently be presented in unit dosage and may be prepared by methods well-known in the pharmaceutical art, by bringing the peptide(s) into association with a carrier or diluent, as a suspension or solution, and optionally one or more accessory ingredients, e.g. buffers, surface active agents, and the like.

The present invention also provides a method for treating or preventing an infection or disease caused by *S. aureus* in a subject comprising administering to the subject one or more of the inhibitor peptides in an amount effective to treat or prevent the infection or disease caused by *S. aureus*. The subject may be human or animal and is preferably is human. The peptide(s) alone, or conjunction with a suitable pharmaceutically acceptable carrier, may be administered by procedures known to those skilled in the art, including but not limited to parenteral (i.e., intravenous, intramuscular, subcutaneous, or intraperitoneal administration), oral, sublingual and topical administration. The actual dose of the peptide(s) administered will depend upon the route of administration, the pharmacokinetics properties of the individual treated, as well as the results desired, and is readily determinable by one skilled in the art. It is also within the confines of the present invention that the peptide(s) may be administered in combination with traditional antibiotics which are used to treat diseases or infections caused by *S. aureus*.

The present invention is described in the following Examples which are set forth to aid in an understanding of the invention, and should not be construed to limit in any way the invention as defined in the claims which follow thereafter.

EXAMPLE 1

Effect of Conditioned-Media of Staphylococci on the Agr Expression of *S. aureus* RN6390B Various culture supernatants from 172 *S. aureus* and 15 other staphylococci were grown in CYGP broth at 37° C. for 6 hours starting at a cell density of 2×10$^9$ cells/ml. Cells were removed by centrifugation at 4° C. The supernatant was boiled for 10 minutes, filtered (0.22 μm filter), centrifuged, filtered with a Centricon 3 filter (3 kDa cutoff). The supernatant from these *S. aureus* strains and other staphylococci were then analyzed using the procedures described in Ji, G., et al. *PNAS USA* 92:12055–12059 (1995) for their ability to activate or inhibit agr transcription of *S. aureus* RN6309B. The results are presented in Tables 1 and 2. These strains can be divided into four groups as follows. In groups I, II and III (all *S. aureus*), the members of any one group produce a substance that activates the virulence response (agr transcription) in any other member of the same group but inhibits the response in any member of either of the other two groups. It is believed that this substance may have activation or inhibition properties depending on the strain being tested. In group IV (several staphylococcal species other than *S. aureus*), each of the members produces a substance that inhibits the response in RN6390B, the standard strain from group I. The substances produced by group IV strains have little or no agr-activating activity with any member of the group.

EXAMPLE 2

Purification of RN6390B *S. Aureus* Peptide Using C18 Reverse Phase HPLC

*S. aureus* strain RN 7668 (pRN6911) was grown in tryptophan assay medium plus 50 μg/ml of L-tryptophan and 5 μg/ml CBAP starting at $2 \times 10^9$ cells/ml. Before use, the medium was dialyzed with a 2 kDA cutoff membrane, discarding the contents of the membrane sac. After 6 hours of growth at 37° C., cells were removed by centrifugation and the culture supernatant was filtered (0.22 μm filter), boiled for 10 minutes, lyophilized and resuspended in 2.5% acetonitrile/ 0.1% trifluoroacetic acid (1/40 volume of the culture supernatant). This material (3 ml) was loaded onto an HPLC C18 column in 2.5% acetonitrile/ 0.1% trifluoroacetic acid, and eluted with an acetonitrile gradient (16–48%) at 0.27% acetonitrile per minute. The collected fractions (1.5 ml per fraction) were lyophilized and suspended in 0.1 ml of 20 mM Tris-HCL buffer (pH 7.5). Fractions with activator pheromone activity were pooled and filtered through a Centricon 3 filter with 3 kDa cutoff. The filtrate (1 ml) was rerun on the HPLC C-18 column and eluted with an acetonitrile gradient at 0.2% acetonitrile per minute over the interest range (20–30%).

The activator peptide, eluting at an acetonitrile 25 concentration of about 28.5%, was analyzed by matrix-assisted laser desorption/ionization mass spectrometry (MALDI-MS) (Hillenkamp, F., et al. *Anal. Chem.* 63:1193A–1203A (1991)) and its amino acid sequence was determined to be Tyr-Ser-Thr-Cys-Asp-Phe-Ile-Met (SEQ ID NO:2) by a Procise Edman Sequencer (Perkin-Elmer), which is located within the AgrD gene as shown in FIG. 2. MALDI-MS was performed using a linear time-of-flight mass spectrometer with a nitrogen laser ion source custom-built at New York University. The matrix used was α-cyano-4-hydroxycinnamic acid and the sample was prepared using the droplet method.

The purified activator peptide was then analyzed for its ability activate and inhibit RNAIII transcription of *S. aureus* strains RN6390B, RN6607 and RN8463, as described in Ji, G., et al. *PNAS USA* 92:12055–12059 (1995). The results are presented in FIG. 3, which show that the activator peptide had an activator effect on strain RN6390B, and an inhibitor effect on strains RN6607 and RN8463.

EXAMPLE 3

Purification of Other *S. Aureus* Peptides Using C18 Reverse Phase HPLC

*S. aureus* strain RN 7667 containing cloned agrBD genes of either RN6607 or RN8463 was grown in tryptophan assay medium plus 50 μg/ml of L-tryptophan and 5 μg/ml CBAP starting at $2 \times 10^9$ cells/ml. After 6 hours of growth, cells were removed by centrifugation and the culture supernatant was filtered (0.22 μm filter), boiled for 10 minutes, lyo- philized and suspended in solution A (2.5% acetonitrile plus 0.1% trifluoroacetic acid). This material was loaded onto a Sephasil C18 (Pharmacia) column (3 cm×5 cm), washed once with solution A, once with solution B (15% acetonitrile plus 0.1% trifluoroacetic acid) and eluted with solution C (40% acetonitrile plus 0.1% trifluoroacetic acid). The eluted material was lyophilized, suspended in 20 mM Tris-HCL buffer (pH 7.5) and filtered through a Centricon 3 filter (Amicon). The filtrate was then loaded onto an HPLC C-18 column and eluted with an acetonitrile gradient (16–32%) at 0.2% acetonitrile per minute. Fractions with activity were pooled, lyophilized, suspended in 20 mM Tris-HCL buffer (pH 7.5) and analyzed by MALDI-MS, and its amino acid sequence was determined by a Perkin-Elmer Procise Edman Sequencer. The amino acid sequences for RN6607 and RN8463 were determined to be Gly-Val-Asn-Ala-Cys-Ser-Ser-Leu-Phe (SEQ ID NO:5) and Tyr-Ile-Asn-Cys-Asp-Phe-Leu-Leu (SEQ ID NO:4), respectively, which are located in the same region of agrD as the activator peptide from *S. aureus* strain RN6390B as shown in FIG. 2.

The purified peptide were then analyzed for their ability activate and inhibit RNAIII transcription of *S. aureus* strains RN6390B, RN6607 and RN8463, as described in Ji, G., et al. *PNAS USA* 92:12055–12059 (1995). The peptide from RN6607 had an activator effect on strain RN6607, and an inhibitor effect on strains RN6390B and RN8463, while the peptide from RN8463 had an activator effect on strain RN8463, and an inhibitor effect on strains RN6390B and RN6607, as shown in FIG. 3.

EXAMPLE 4

Purification and Analysis of Inhibitor Peptide From *S. lugdunensis*

*S. aureus* strain RN 7668 (pSLBD) was grown in methionine assay medium plus 50 μg/ml of L-methionine and 5 μg/ml CBAP starting at $2 \times 10^9$ cells/ml. Before use, the medium was dialyzed with a 2 kDA cutoff membrane, discarding the contents of the membrane sac. After 6 hours of growth at 37° C., cells were removed by centrifugation and the culture supernatant was boiled for 10 minutes and filtered (0.22 μm filter). This material was loaded onto a Sephasil C18 column (3.5×4 cm), washed with (i) 2.5% acetonitrile, 0.1% trifluoroacetic acid, (ii) 10.5% acetonitrile, 0.1% trifluoroacetic acid. The inhibitor was eluted with 42.5% acetonitrile, 0.1% trifluoroacetic acid, lyophilized, suspended in 20 mM Tris-HCl buffer (pH 7.5) and filtered through a Centricon 3 filter with a 3 kDa cutoff. This material was then loaded onto an HPLC C-18 column and eluted with an acetonitrile gradient. Fractions with inhibitor pheromone activity were pooled, lyophilized, dissolved in 20 mM Tris-HCL buffer (pH 7.5) and stored at −80° C. The fractions were analyzed by MALDI-MS, and using Edman degradation procedure, this peptide was determined to have the amino sequence Asp-Ile-Cys-Asn-Ala-Tyr-Phe, which is located in the same region of agrD as the activator peptide from *S. aureus* strain RN6390B as shown in FIG. 2.

The purified *S. lugdunensis* pheromone was then analyzed for its ability activate and inhibit RNAIII transcription of various *S. aureus* strains. *S. aureus* strains were grown to 30

Klett units (for activation assays) and to 60 Klett units (for inhibition assays). The purified S. *lugdunensis* pheromone was added and the mixtures were incubated at 37° C. for 30 minutes. Whole cell lysates were prepared from these cultures and analyzed by Northern blot hybridization using a RN6390B RNAIII-specific probe. The S. *lugdunensis* pheromone inhibits the agr response in 5 of 6 S. *aureus* strains tested as shown in FIGS. 4A and 4B.

EXAMPLE 5

Commercial Synthesis of Synthetic Peptide Corresponding to RN6390B and S. *luadunensis* Sequences Peptides having the same amino acid sequences as the native peptides from RN6390B and S. *lugdunensis* were synthesized commercially (Yale University, New Haven, Conn.) and analyzed by MALDI-MS. Unlike the purified peptides, the synthesized peptides did not have activity. Mass spectroscopy showed that the synthetic peptides were dimeric, whereas the native peptide molecules were monomeric and had molecular masses that were 18±1 atomic mass units less than those predicted by their respective amino acid sequences. Taken together, these results suggest that the cysteines in the synthetic peptides had spontaneously formed intermolecular disulfides, whereas those in the native peptides were involved in an intramolecular bond, most likely a cyclic thioester introduced post-translationally and involving the C-terminal carboxyl, since there is no other conserved carboxyl group in the molecule. Consistent with this possibility were the results of treatment of the native peptides with iodoacetic acid and hydroxylamine. Iodoacetic acid, expected to react with free -SH groups, had no effect, whereas hydroxylamine, expected to react with thioesters, abolished activity.

have shown that the synthetic material inhibits agr expression by RN6390B. It is expected that the introduction of the cyclic thioester bond to the other peptide will have a similar effect on activity.

TABLE 1

Effect of Conditioned-Media of Staphylococci on the Agr Expression of S. *aureus* RN6390B

| Strains | Activation | Inhibition |
| --- | --- | --- |
| S. *aureus* | | |
| Animal Mastitis Isolates (6) | 4 | 2 |
| Capsule Strains (3) | 0 | 3 |
| Clinical Isolates (39) | 17 | 22 |
| Coag (9) | 0 | 9 |
| Laboratory Strains (4) | 1 | 3 |
| MRSA (65) | 13 | 52 |
| TSST-1[+] (46) | 3 | 43 |
| S. *capitis*, S. *caprae*, S. *carnosus*, S. *caseolyticus*, S. *epidermidis*, S. *haemolyticus*, S. *hominis*, S. *hyicus* subsp. *hyicus*, S. *hyicus* subsp. *chromo*, S. *kloosii*, S. *lentus*, S. *lugdunensis*, S. *sciuri*, S. *simulans*, S. *xylosus* | 0 | All |

TABLE 2

Effect of conditioned-media on S. *aureus* Agr expression

| | Supernatant Added | | | | | | |
| --- | --- | --- | --- | --- | --- | --- | --- |
| | RN6390B | RN6596 | RN7690 | RN6607 | RN7843 | RN8462 | RN8463 |
| Strains Used for Assays | | | | | | | |
| RN6390B | + | + | + | − | − | − | − |
| RN6596 | + | + | + | − | − | − | − |
| RN7690 | + | + | + | − | − | − | − |
| RN6607 | − | − | − | + | − | − | − |
| RN7843 | − | − | − | − | + | + | + |
| RN8462 | − | − | − | − | + | + | + |
| RN8463 | − | − | − | − | + | + | + |

Note:
+ Activation
− Inhibition
Group:
(1) RN6390, RN6596, RN7690
(2) RN6607
(3) RN7843, RN8462, RN8463

EXAMPLE 6

Synthesis of a Synthetic Peptide Corresponding to the RN8463 Sequence

We have succeeded in synthesizing a small quantity of a cyclic thioester derivative of the RN8463 octapeptide and All publications mentioned hereinabove are hereby incorporated by reference in their entirety.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention in the appended claims.

What is claimed is:

1. A purified peptide characterized as:
   (i) inhibiting or activating agr-rnaIII transcription in *S. aureus*; and
   (ii) consisting of about six to about twelve amino acids in length;
      wherein the about six to about twelve amino acids comprise a sequence with a cysteine residue from an AgrD region of a staphylococci bacterium, the sequence selected from the group consisting of:
      (a) Asp-Ile-Cys-Asn-Ala-Tyr-Phe (SEQ ID NO:1);
      (b) Tyr-Ser-Thr-Cys-Asp-Phe-Ile-Met (SEQ ID NO:2);
      (c) Gly-Val-Asn-Ala-Cys-Ser-Ser-Leu-Phe (SEQ ID NO:3); and
      (d) Tyr-Ile-Asn-Cys-Asp-Phe-Leu-Leu (SEQ ID NO:4).

2. The peptide of claim 1, which is isolated from the AgrD region of *S. lugdunensis*.

3. The peptide of claim 2, wherein the about six to about twelve amino acids comprise the amino acid sequence Asp-Ile-Cys-Asn-Ala-Tyr-Phe (SEQ ID NO:1).

4. The peptide of claim 3, consisting of the amino acid sequence NH₂-Asp-Ile-Cys-Asn-Ala-Tyr-Phe-COOH (SEQ ID NO:1) and a cyclic thioester bond between Cys and COOH.

5. The peptide of claim 1, which is isolated from the AgrD region of *S. aureus*.

6. The peptide of claim 5, wherein the about six to about twelve amino acids comprise the amino acid sequence Tyr-Ser-Thr-Cys-Asp-Phe-Ile-Met (SEQ ID NO:2).

7. The peptide of claim 5, wherein the about six to about twelve amino acids comprise the amino acid sequence Gly-Val-Asn-Ala-Cys-Ser-Ser-Leu-Phe (SEQ ID NO:3).

8. The peptide of claim 5, wherein the about six to about twelve amino acids comprise the amino acid sequence Tyr-Ile-Asn-Cys-Asp-Phe-Leu-Leu (SEQ ID NO:4).

9. The peptide of claim 6, consisting of the amino acid sequence NH₂-Tyr-Ser-Thr-Cys-Asp-Phe-Ile-Met-COOH (SEQ ID NO:2) and a cyclic thioester bond between Cys and COOH.

10. The peptide of claim 7, consisting of the amino acid sequence NH$_2$-Gly-Val-Asn-Ala-Cys-Ser-Ser-Leu-Phe-COOH (SEQ ID NO:3) and a cyclic thioester bond between Cys and COOH.

11. The peptide of claim 8, consisting of the amino acid sequence NH$_2$-Tyr-Ile-Asn-Cys-Asp-Phe-Leu-Leu-COOH (SEQ ID NO:4) and a cyclic thioester bond between Cys and COOH.

12. The peptide of claim 1, which is isolated from a staphylococci bacterium, recombinantly produced or chemically synthesized.

13. The purified peptide of claim 1, further comprising a cyclic thioester bond between the cysteine residue and a C-terminal carboxyl.

14. The purified peptide of claim 3, further comprising a cyclic thioester bond between the cysteine residue and a C-terminal carboxyl.

15. The purified peptide of claim 6, further comprising a cyclic thioester bond between the cysteine residue and a C-terminal carboxyl.

16. The purified peptide of claim 7, further comprising a cyclic thioester bond between the cysteine residue and a C-terminal carboxyl.

17. The purified peptide of claim 8, further comprising a cyclic thioester bond between the cysteine residue and a C-terminal carboxyl.

* * * * *

SEQUENCE LISTING

```
<160> NUMBER OF SEQ ID NOS: 8

<210> SEQ ID NO 1
<211> LENGTH: 7
<212> TYPE: PRT
<213> ORGANISM: Staphylococcus lugdunensis

<400> SEQUENCE: 1

Asp Ile Cys Asn Ala Tyr Phe
1               5

<210> SEQ ID NO 2
<211> LENGTH: 8
<212> TYPE: PRT
<213> ORGANISM: Staphylococcus aureus

<400> SEQUENCE: 2

Tyr Ser Thr Cys Asp Phe Ile Met
1               5

<210> SEQ ID NO 3
<211> LENGTH: 9
<212> TYPE: PRT
<213> ORGANISM: Staphylococcus aureus

<400> SEQUENCE: 3

Gly Val Asn Ala Cys Ser Ser Leu Phe
1               5

<210> SEQ ID NO 4
<211> LENGTH: 8
<212> TYPE: PRT
<213> ORGANISM: Staphylococcus aureus

<400> SEQUENCE: 4

Tyr Ile Asn Cys Asp Phe Leu Leu
1               5

<210> SEQ ID NO 5
<211> LENGTH: 46
<212> TYPE: PRT
<213> ORGANISM: Staphylococcus aureus

<400> SEQUENCE: 5

Met Asn Thr Leu Phe Asn Leu Phe Phe Asp Phe Ile Thr Gly Ile Leu
1               5                   10                  15

Lys Asn Ile Gly Asn Ile Ala Ala Tyr Ser Thr Cys Asp Phe Ile Met
                20                  25                  30

Asp Glu Val Glu Val Pro Lys Glu Leu Thr Gln Leu His Glu
            35                  40                  45

<210> SEQ ID NO 6
<211> LENGTH: 47
<212> TYPE: PRT
<213> ORGANISM: Staphylococcus aureus
```

-continued

```
<400> SEQUENCE: 6

Met Asn Thr Leu Val Asn Met Phe Phe Asp Phe Ile Ile Lys Leu Ala
1               5                  10                  15

Lys Ala Ile Gly Ile Val Gly Gly Val Asn Ala Cys Ser Ser Leu Phe
             20                  25                  30

Asp Glu Pro Lys Val Pro Ala Glu Leu Thr Asn Leu Tyr Asp Lys
         35                  40                  45

<210> SEQ ID NO 7
<211> LENGTH: 46
<212> TYPE: PRT
<213> ORGANISM: Staphylococcus aureus

<400> SEQUENCE: 7

Met Lys Lys Leu Leu Asn Lys Val Ile Glu Leu Leu Val Asp Phe Phe
1               5                  10                  15

Asn Ser Ile Gly Tyr Arg Ala Ala Tyr Ile Asn Cys Asp Phe Leu Leu
             20                  25                  30

Asp Glu Ala Glu Val Pro Lys Glu Leu Thr Gln Leu His Glu
         35                  40                  45

<210> SEQ ID NO 8
<211> LENGTH: 53
<212> TYPE: PRT
<213> ORGANISM: Staphylococcus lugdunensis

<400> SEQUENCE: 8

Met Asn Leu Leu Ser Gly Leu Phe Thr Lys Gly Ile Ser Ala Ile Phe
1               5                  10                  15

Glu Phe Ile Gly Asn Phe Ser Ala Gln Asp Ile Cys Asn Ala Tyr Phe
             20                  25                  30

Asp Glu Pro Glu Val Pro Gln Glu Leu Ile Asp Leu Gln Arg Lys Gln
         35                  40                  45

Leu Ile Glu Ser Val
     50
```